US00PP36769P2

(12) United States Plant Patent
Bruinen

(10) Patent No.: US PP36,769 P2
(45) Date of Patent: Jun. 24, 2025

(54) ***ZAMIOCULCAS* PLANT NAMED 'EDZAM2203'**

(50) Latin Name: *Zamioculcas zamiifolia (hort. Lodd.) Engl.*
Varietal Denomination: EDZAM2203

(71) Applicant: Ed Holding B.V., Maasdijk (NL)

(72) Inventor: Ed Bruinen, Maasdijk (NL)

(73) Assignee: Ed Holding B.V., Maasdijk (NL)

( * ) Notice: Subject to any disclaimer, the term of this patent is extended or adjusted under 35 U.S.C. 154(b) by 0 days.

(21) Appl. No.: 18/831,288

(22) Filed: Oct. 17, 2024

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/00; A01H 5/12
See application file for complete search history.

*Primary Examiner* — Kent L Bell
(74) *Attorney, Agent, or Firm* — Samuel R. McCoy, Jr.

(57) ABSTRACT

'EDZAM2203' is a new and distinctive *Zamioculcas* plant which is characterized by an abundance of foliage with a large number of erect leaflets born on long petioles, mid-green leaflets, and a dark yellow-green petiole that is blotched with greyed-green. The new plant propagates successfully by leaf cuttings and has shown to be uniform and stable in the resulting generations from asexual propagation.

2 Drawing Sheets

Latin name of the genus and species: The Latin name of the genus and species of the novel variety disclosed herein is *Zamioculcas zamiifolia* (hort. Lodd.) Engl.

Variety denomination: The inventive variety of *Zamioculcas* disclosed herein has been given the variety denomination 'EDZAM2203'.

BACKGROUND OF THE INVENTION

Parentage: 'EDZAM2203' is a seedling selection resulting from the controlled pollination of *Zamioculcas zamiifolia* 'AS1' (unpatented), the seed parent, with *Zamioculcas zamiifolia* 'MK2' (unpatented), the pollen parent, at a commercial nursery in Maasdijk, The Netherlands, in the summer of 2015. Both parents were developed and owned by the inventor and were never released to the public or otherwise made commercially available. In the summer of 2017, one plant was observed to exhibit an abundance of foliage and unique growth habit characteristics and was isolated for further evaluation in order to confirm the distinctness and stability of the characteristics first observed. Upon confirmation of distinctness and stability, 'EDZAM2203' was selected for commercialization.

Asexual Reproduction: Asexual reproduction of 'EDZAM2203' was first accomplished in summer of 2017 by way of stem cuttings at a commercial greenhouse in Maasdijk, The Netherlands. Four successive generations produced from stem cuttings have shown that the unique features of the instant cultivar are stable and reproduce true to type.

SUMMARY OF THE INVENTION

The cultivar 'EDZAM2203' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Zamioculcas* plant, 'EDZAM2203'. These traits, in combination, distinguish 'EDZAM2203' as a new and distinct cultivar.

1. *Zamioculcas* 'EDZAM2203' exhibits an abundance of foliage with a large number of very erect leaflets born on long petioles; and
2. *Zamioculcas* 'EDZAM2203' exhibits mid-green, elliptic to oblong leaflets; and
3. *Zamioculcas* 'EDZAM2203' exhibits dark yellow-green petioles with greyed-green blotches.

BOTANICAL DESCRIPTION OF THE PLANT

Figure 1:
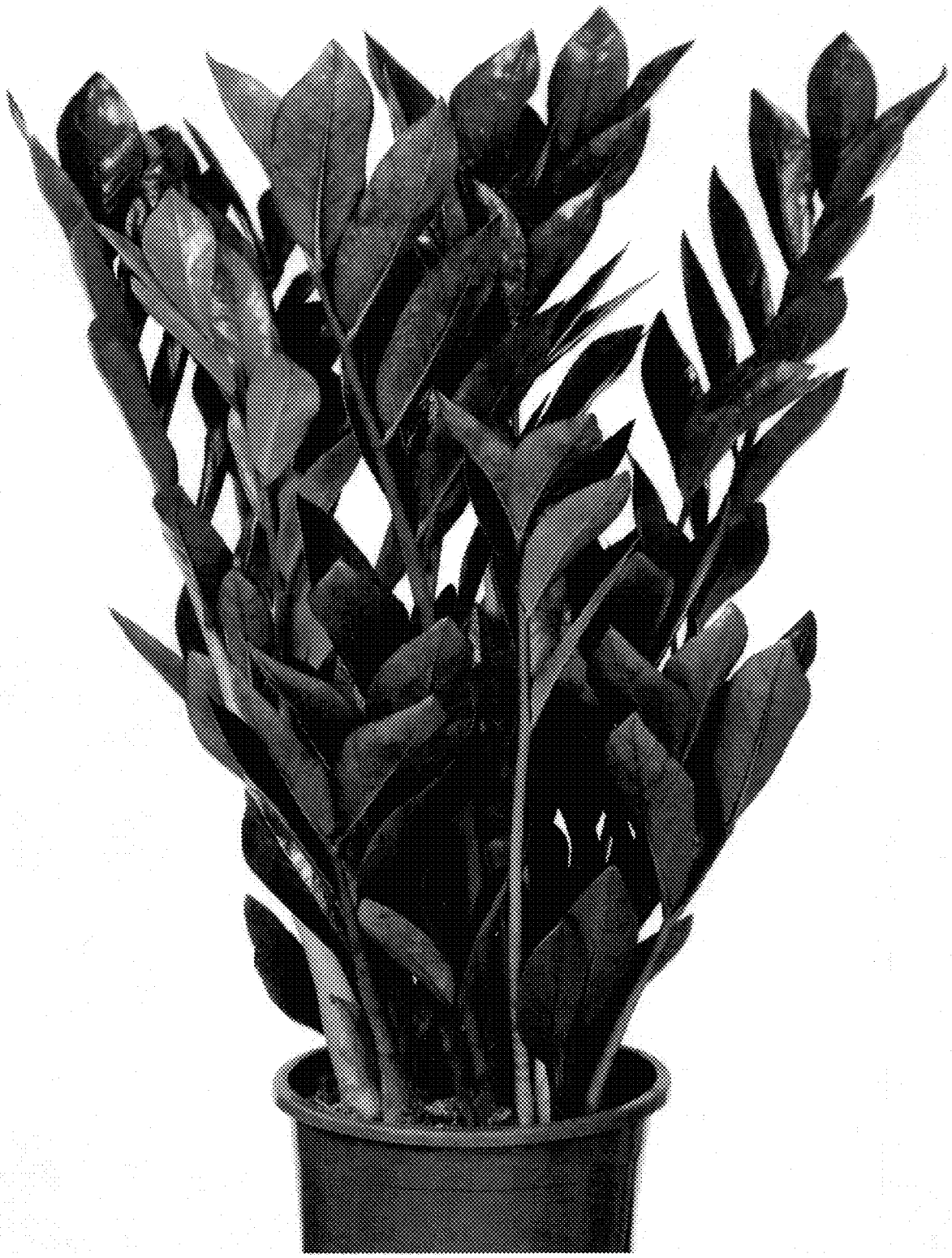
FIG. 1 shows, as nearly true as it is reasonably possible to make the same in color illustrations of this type, the typical foliage and growth characteristics of the new cultivar, 'EDZAM2203'. The plant shown is approximately 12 months old, potted into a 15 cm nursery pot, grown at a commercial greenhouse in Maasdijk, The Netherlands.
Figure 2:
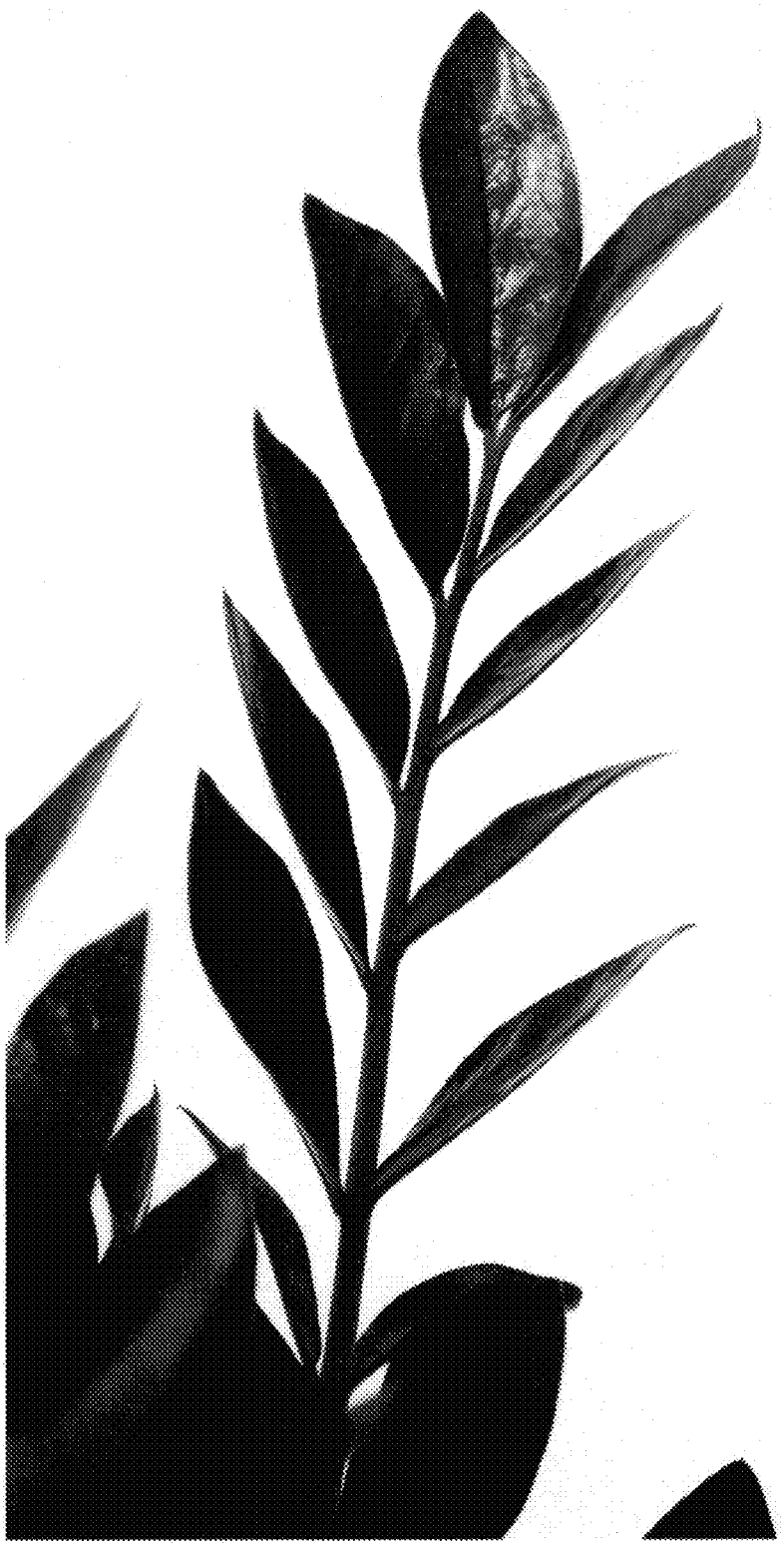
FIG. 2 shows, as nearly true as it is reasonably possible to make the same in color illustrations of this type, the typical foliage of the plant in FIG. 1.

The following is a detailed botanical description of a new and distinct variety of *Zamioculcas zamiifolia* known as 'EDZAM2203', based upon observations of 12-month-old plants, potted into 15 cm nursery pots and grown indoors at a commercial nursery in Maasdijk, The Netherlands. Plants were grown in full sun using accepted fertility, to include supplemental Calcium applications, and irrigation practices for *Zamioculcas* plants. With the exception of preventative fungicides, no chemical pest control measures were employed. Furthermore, no artificial light or photoperiodic treatments were given to the plants. Observation data was recorded in October of 2023.

Those skilled in the art will appreciate that certain characteristics will vary with older or, conversely, with younger plants. 'EDZAM2203' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, sixth edition, 2015.

A botanical description of 'EDZAM2203' and comparisons with the parent plants and the most similar variety of common knowledge are provided below.

General plant description:

*Growth habit*.—Tropical evergreen perennial.

*Plant profile shape*.—Inverted triangular.

*Growth rate*.—Moderately fast growing.

*Plant vigor*.—Moderately vigorous.

*Height*.—48.0 cm to the top of the foliar plane.

*Width*.—41.5 cm.

*Propagation*.—Type — Leaf cuttings. Time to initiate rooting — Approximately 30 days at an approximate temperature of 25 degrees Celsius. Crop time — Approximately 1 year to produce a marketable plant in a 12 cm container.

*Pathogen and pest resistance and susceptibility*.—Plants have not been observed to be susceptible or resistant to pathogens and pests common to *Zamioculcas* sp.

*Environmental tolerances*.—Adapt to, at least, USDA Zones 10 to 12 and temperatures ranging from 5 to 40 degrees Celsius; moderate tolerance to rain; low tolerance to wind.

Stem:

*Branching habit*.—No stems or branches; compound leaves in small clumps, arising directly from tuberous rhizomes.

*Number of clumps per plant*.—Five, on average.

*Number of additional clumps formed each year*.—Five, on average.

Root system:

*Type*.—Tuberous rhizomes bearing thick fleshy roots.

*Shape of rhizomes*.—Irregular broad oblong to ovoid.

*Dimensions of rhizomes*.—5.0 cm long and 3.7 cm in diameter.

*Density of rhizomes and roots*.—Moderately dense.

*Distribution of rhizomes and roots*.—Rhizomes shallow; roots distributed evenly throughout the soil profile, from shallow to deep.

*Texture of rhizomes and roots*.—Glabrous and very fleshy.

*Color of rhizomes and roots*.—Greyed-green, nearest to RHS 197B.

Foliage:

*Arrangement*.—Compound leaves in small clumps, arising directly from tuberous rhizomes.

*Attachment*.—Petiolate.

*Division*.—Pinnately compound.

*Leaf profile shape*.—Narrow oblong.

*Dimensions*.—46.9 cm long and 10.8 cm wide.

*Attitude*.—Near upright; approximately 17.5 degrees from vertical.

*Aspect*.—Carinate.

*Quantity*.—Approximately 5 leaves per clump.

*Stipules*.—General — A leafy stipule is present at the base of each pinnately compound leaf. Shape — Ovate to lanceolate. Length — 10.0 cm. Width — 3.4 cm. Apex — Mucronulate. Base — Broad cuneate. Margin — Entire, moderately undulated. Texture — Papery. Color, adaxial and abaxial surfaces — Translucent greyed-yellow, nearest to RHS 162C, and suffused with grey-brown, nearest to RHS 199D yet lighter; becoming greyed-orange towards the apex, nearest to RHS 177B, and grey-brown, RHS 199C, towards the base.

Petiole:

*Aspect*.—Terete; basal portion of the petiole swollen.

*Length*.—38.6 cm, including the swollen portion of the petiole; the swollen portion is 6.8 cm long.

*Diameter*.—2.0 cm at the base; 0.7 cm below the first leaflet.

*Strength*.—Strong.

*Texture*.—Smooth and glabrous.

*Luster*.—Matte.

*Color, adaxial and abaxial surfaces*.—Yellow-green, nearest to RHS 148A, and sparsely blotched with greyed-green, nearest to in between RHS 197A and 197B.

Rachis:

*Aspect*.—Elliptic.

*Length*.—38.6 cm, including the geniculum.

*Diameter*.—1.0 cm at the widest point; 0.7 cm at the narrowest point.

*Strength*.—Strong.

*Texture*.—Smooth and glabrous.

*Luster*.—Matte.

*Color, adaxial surface*.—Yellow-green, nearest to RHS 148B, and strongly suffused with grey, distally, nearest to RHS 201A; sparsely blotched with greyed-green, nearest to in between RHS 197A and 197B.

*Color, abaxial surface*.—Yellow-green, nearest to RHS 148B, and strongly suffused with grey, distally, nearest to RHS 201A; sparsely blotched with greyed-green, nearest to in between RHS 197A and 197B.

Leaflets:

*Quantity*.—Typically 11 leaflets but ranging from 9 to 12.

*Attitude*.—At an angle of approximately 40 degrees to the rachis.

*Dimensions*.—10.4 cm long and 4.0 cm wide.

*Shape*.—Elliptic to obovate.

*Aspect*.—Slightly carinate and lightly curled inward.

*Apex*.—Acute with a mucronulate tip.

*Base*.—Attenuate.

*Margin*.—Entire; very slightly undulated.

*Texture, adaxial surface*.—Glabrous and moderately coriaceous.

*Texture, abaxial surface*.—Glabrous and moderately coriaceous.

*Luster, adaxial surface*.—Very glossy.

*Luster, abaxial surface*.—Very glossy.

*Color*.—Juvenile foliage color, adaxial surface — Yellow-green, nearest to in between RHS 146A and 147A yet darker; main vein is brown, nearest to RHS 200A. Juvenile foliage color, abaxial surface —

Yellow-green, nearest to RHS 146A; main vein is lighter, nearest to RHS 146D. Mature leaf color, adaxial surface — Nearest to a mixture of green and yellow-green, RHS 139A and 147A yet darker. Mature leaf color, abaxial surface — Yellow-green, nearest to RHS 146A.

Venation:

*Pattern*.—Pinnate.

*Vein color, adaxial surface*.—Yellow-green, nearest to RHS 144A, and suffused with black proximally, nearest to RHS 203B.

*Vein color, abaxial surface*.—Yellow-green, nearest to RHS 146D, and suffused with greyed-green proximally, nearest to in between RHS 197A and 197B.

Petiolule:

*Aspect*.—Flattened elliptic.

*Length*.—0.7 cm.

*Diameter*.—Petiolules flattened; average width is 0.40 cm, and the average height is 0.35 cm.

*Strength*.—Strong.

*Texture, adaxial and abaxial surfaces*.—Smooth and glabrous.

*Luster, adaxial and abaxial surfaces*.—Matte.

*Color, adaxial surface*.—Yellow-green, nearest to RHS 148A.

*Color, abaxial surface*.—Yellow-green, nearest to RHS 146A.

Inflorescence: No flowering has been observed to date.

Comparison with the Parent Plants

Plants of the new cultivar 'EDZAM2203' may be distinguished from its seed parent, *Zamioculcas zamiifolia* 'AS1' (unpatented), by the characteristics described in Table 1.

TABLE 1

Comparison Between 'EDZAM2203' and The Seed Parent

| Characteristic | 'EDZAM2203' | 'ASE' |
|---|---|---|
| Amount of leaf-bearing clumps per plant. | Fewer clumps, and subsequently less foliage, than 'ASI'. | More clumps, and subsequently more foliage per plant, relative to 'EDZAM2203', |
| Leaflet shape. | Elliptic to obovate, yet more towards obovate when compared to 'ASI'. | Elliptic to obovate, yet more towards elliptic when compared to 'EDZAM2203' |
| General coloration of the leaflets. | Lighter shade of green compared to the parent. | Darker shade of green compared to 'EDZAM2203'. |

Plants of the new cultivar 'EDZAM2203' may be distinguished from its pollen parent, *Zamioculcas zamiifolia* 'MK2' (unpatented), by the characteristics described in Table 2.

TABLE 2

Comparison Between 'EDZAM2203' and The Pollen Parent

| Characteristic | 'EDZAM2203' | 'MK2' |
|---|---|---|
| Amount of leaf-bearing clumps per plant, | More clumps, and subsequently more foliage, than 'MK2'. | Fewer clumps and less foliage per plant than 'EDZAM2203'. |
| Leaflet shape. | Elliptic to obovate, yet more towards elliptic when compared to 'MK2'. | Elliptic to obovate, yet more towards obovate when compared to 'EDZAM2203' |
| General coloration of the leaflets, | Darker shade of green compared to 'MK2'. | Lighter shade of green compared to 'EDZAM2203', |

Comparisons with the Most Similar Variety of Common Knowledge

Plants of the new cultivar 'EDZAM2203' are most similar to the commercial variety, *Zamioculcas* 'EDZAM1702' (U.S. Plant Pat. No. 33,429). A comparison of 'EDZAM2203' with 'EDZAM1702' is described in Table 3.

TABLE 3

Comparison Between 'EDZAM2203' and 'EDZAM1702'

| Characteristic | 'EDZAM2203' | 'EDZAM1702' |
|---|---|---|
| Amount of leaf-bearing clumps per plant. | More clumps, and subsequently more foliage, than 'EDZAM1702'. | Fewer clumps and less foliage per plant than 'EDZAM2203'. |
| Leaflet attitude. | More upright than 'EDZAM1702'. | More relaxed than 'EDZAM2203'. |
| Leaflet shape. | Elliptic to oblovate, yet more towards elliptic, when compared to 'EDZAM1702'. | Obovate to elliptic, yet more towards obovate when compared to 'EDZAM2203'. |
| General coloration of the leaflets. | Darker shade of green compared to 'EDZAM1702'. | Lighter shade of green compared to 'EDZAM2203'. |

That which is claimed is:

1. A new and distinct variety of *Zamioculcas* plant named 'EDZAM2203', substantially as described and illustrated herein.

* * * * *